US008726510B2

(12) United States Patent
Voudouris

(10) Patent No.: US 8,726,510 B2
(45) Date of Patent: May 20, 2014

(54) METHOD OF MAKING A CLIP FOR A SELF-LIGATING ORTHODONTIC BRACKET

(76) Inventor: John C. Voudouris, Toronto (CA)

( * ) Notice: Subject to any disclaimer, the term of this patent is extended or adjusted under 35 U.S.C. 154(b) by 0 days.

(21) Appl. No.: 12/558,910

(22) Filed: Sep. 14, 2009

(65) Prior Publication Data

US 2010/0000069 A1    Jan. 7, 2010

Related U.S. Application Data

(63) Continuation of application No. 11/697,312, filed on Apr. 6, 2007, now abandoned, which is a continuation-in-part of application No. 10/592,184, filed as application No. PCT/CA2005/000366 on Mar. 8, 2005, now abandoned.

(60) Provisional application No. 60/909,609, filed on Apr. 2, 2007, provisional application No. 60/551,281, filed on Mar. 8, 2004.

(51) Int. Cl.
B23P 13/00 (2006.01)
A61C 7/30 (2006.01)
B22D 11/128 (2006.01)

(52) U.S. Cl.
USPC ..... 29/896.11; 29/896.1; 29/527.1; 29/527.2; 433/11

(58) Field of Classification Search
USPC .............. 29/896.11, 896.1, 527.2, 527.1; 433/8–12
See application file for complete search history.

(56) References Cited

U.S. PATENT DOCUMENTS

| 4,712,999 | A | * | 12/1987 | Rosenberg | 433/8 |
| 4,842,513 | A | | 6/1989 | Haarmann | |
| 5,252,066 | A | | 10/1993 | Fairhurst | |
| 5,263,858 | A | * | 11/1993 | Yoshida et al. | 433/8 |
| 5,295,823 | A | | 3/1994 | Farzin-Nia | |
| 5,630,715 | A | * | 5/1997 | Voudouris | 433/8 |
| 5,857,849 | A | * | 1/1999 | Kurz | 433/10 |
| 5,913,680 | A | | 6/1999 | Voudouris | |
| 5,944,517 | A | | 8/1999 | Binder | |
| 6,142,775 | A | | 11/2000 | Hansen et al. | |
| 6,264,469 | B1 | | 7/2001 | Moschik | |
| 6,648,638 | B2 | | 11/2003 | Castro et al. | |
| 6,910,884 | B2 | * | 6/2005 | Kelly et al. | 433/9 |
| 2004/0121278 | A1 | | 6/2004 | Kelly et al. | |
| 2004/0146835 | A1 | | 7/2004 | Ihde | |
| 2006/0172247 | A1 | | 8/2006 | Abels et al. | |

FOREIGN PATENT DOCUMENTS

WO    WO 9633837 A1 * 10/1996  ............ B23K 15/08
WO    2005084575           9/2005

OTHER PUBLICATIONS

International Search Report and Written Opinion issued on Jun. 29, 2006 for International Application No. PCT/CA2005/000366.
European Search Report issued on Jul. 17, 2008 for European Patent Application No. EP08006379.

* cited by examiner

Primary Examiner — Sarang Afzali
(74) Attorney, Agent, or Firm — Fox Rothschild LLP

(57) ABSTRACT

An orthodontic bracket having a body having an archwire slot and adapted to be secured to a tooth, and a clip coupled to the body and movable between an open position, permitting access to the archwire slot, and a closed position, inhibiting access to the archwire slot. The clip has a base material having recesses formed by laser-ablation, and a coating formed over at least one of the recesses.

6 Claims, 10 Drawing Sheets

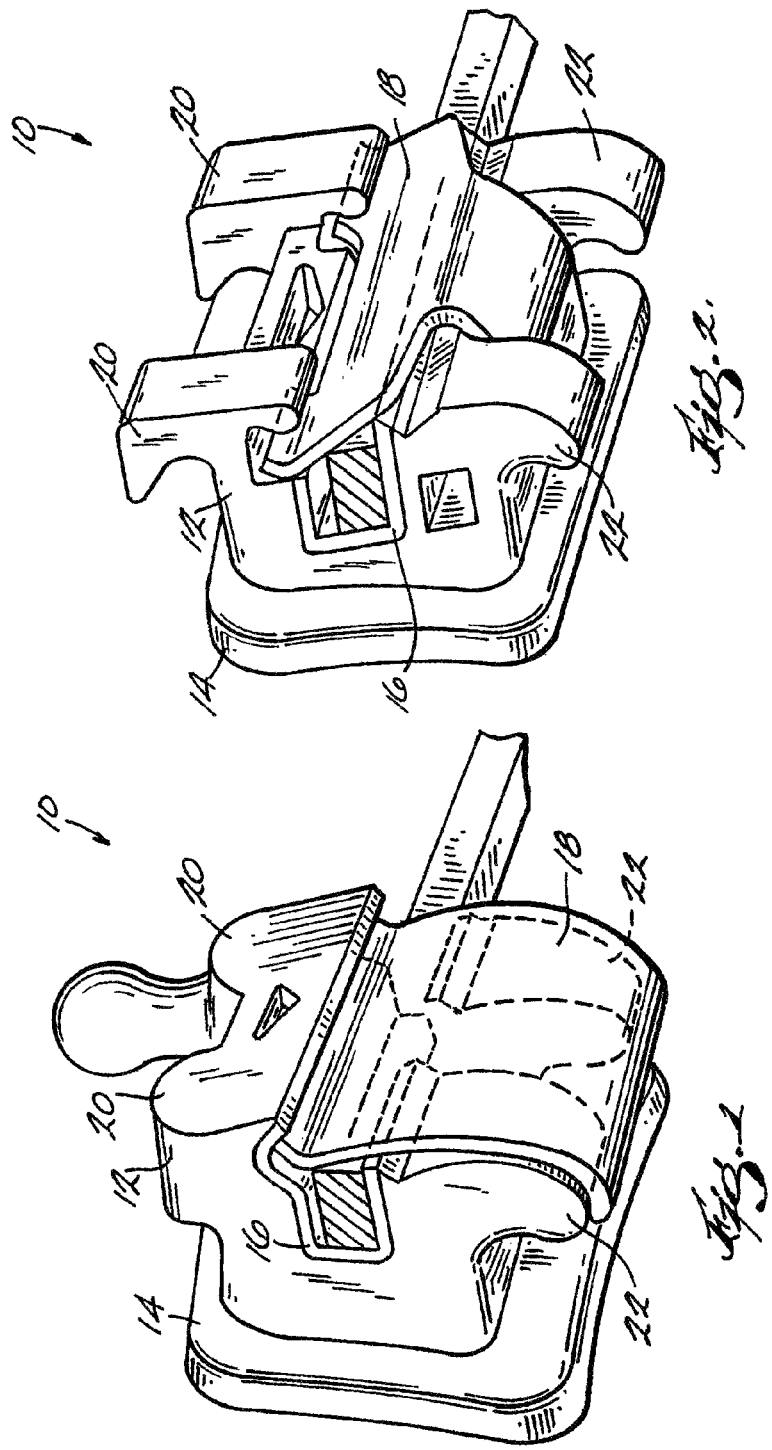

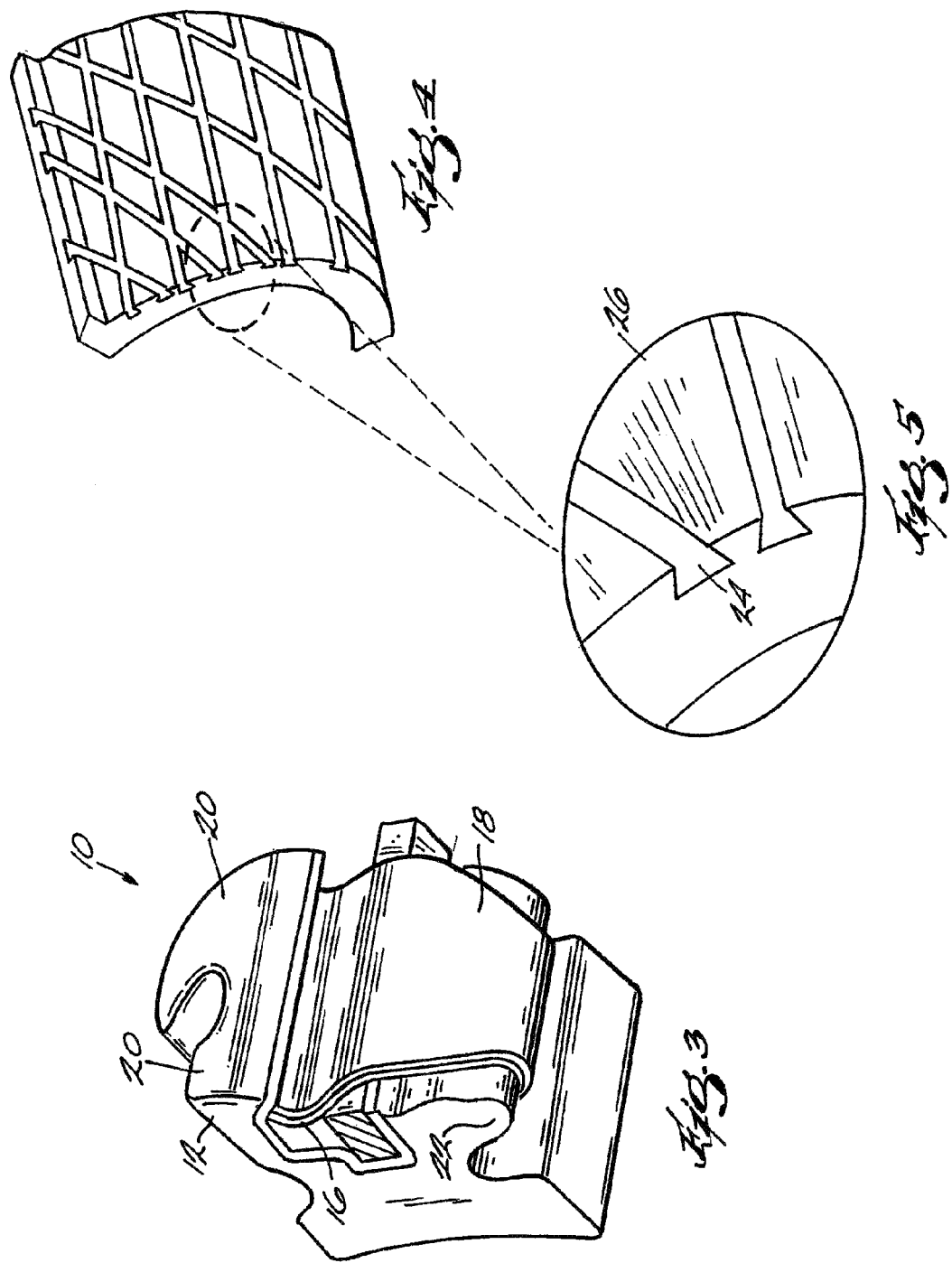

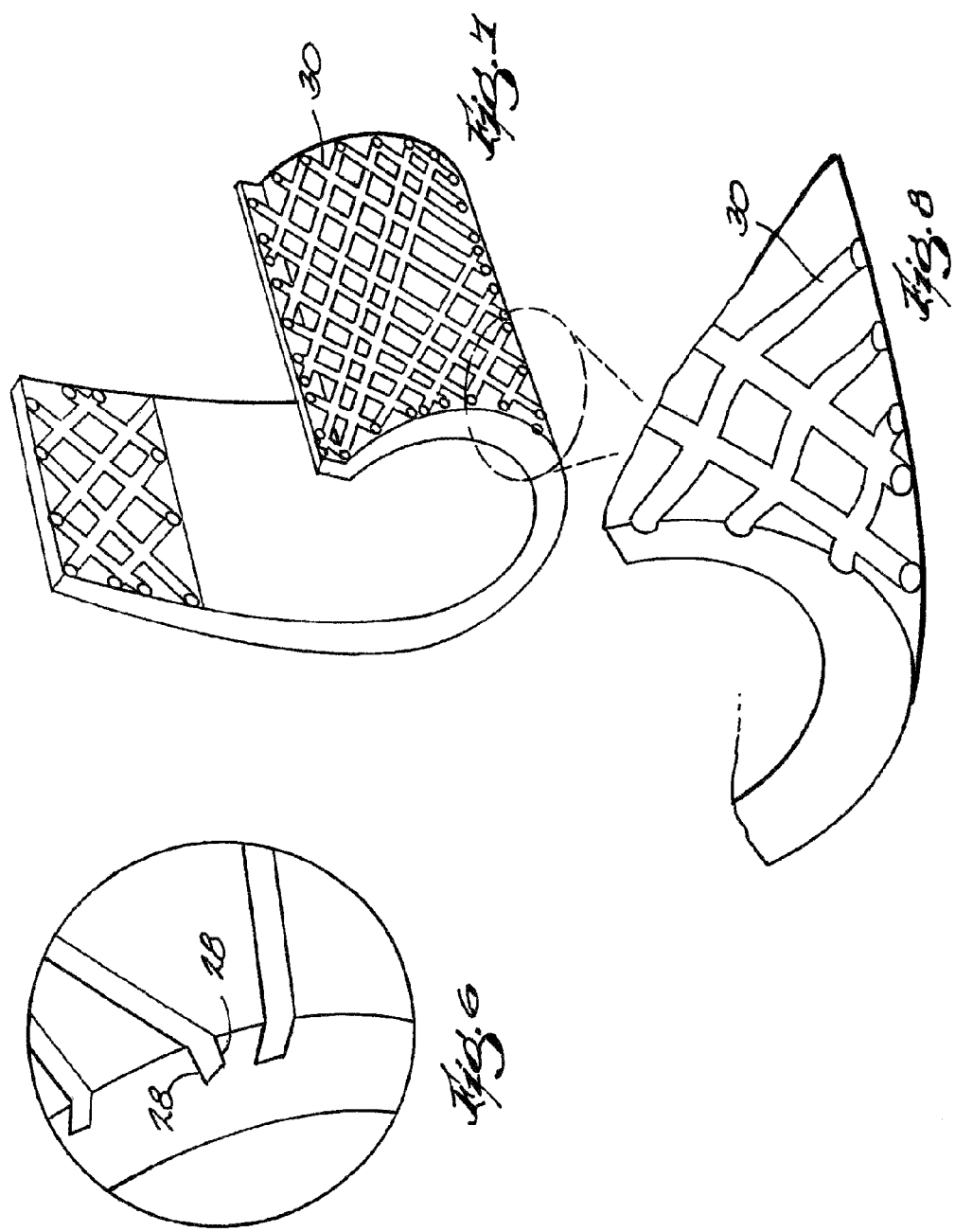

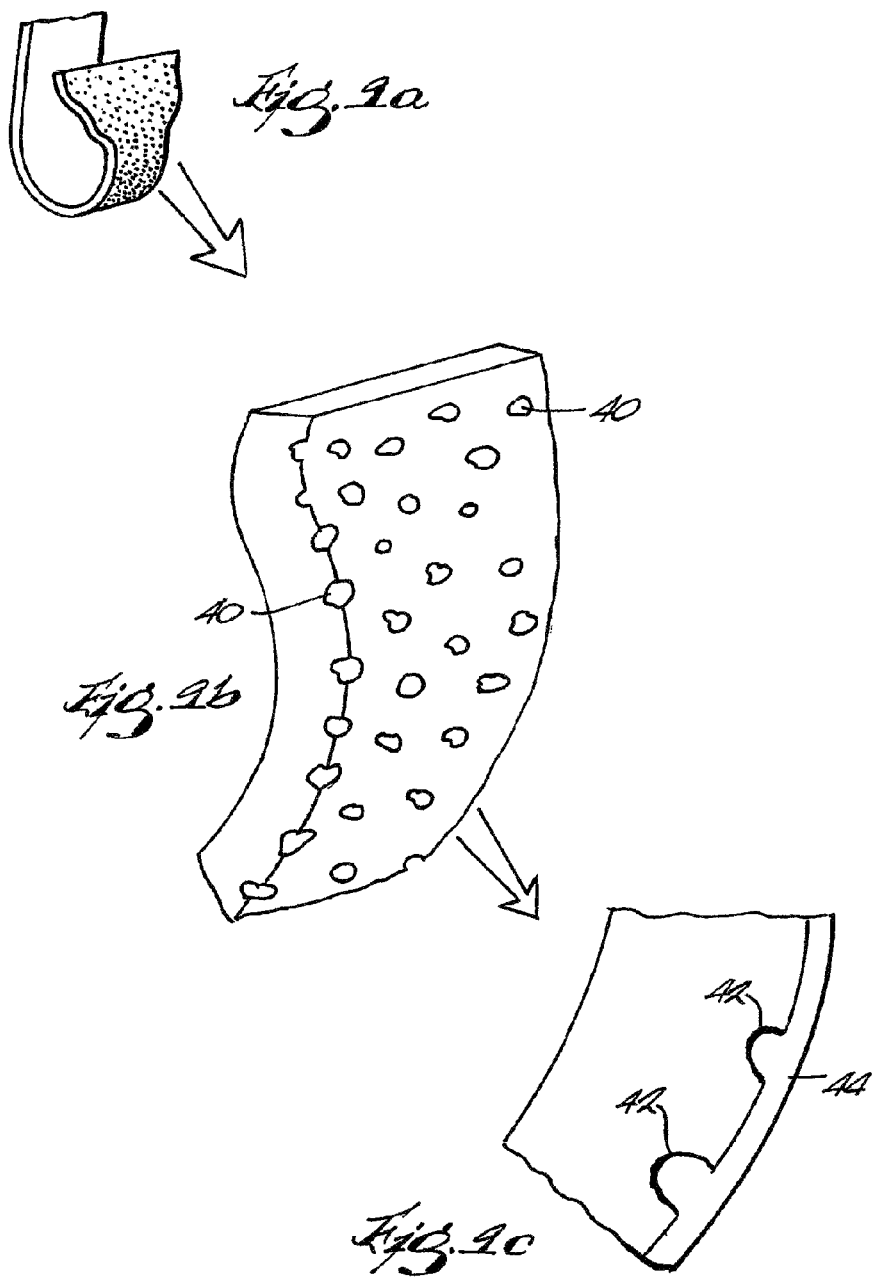

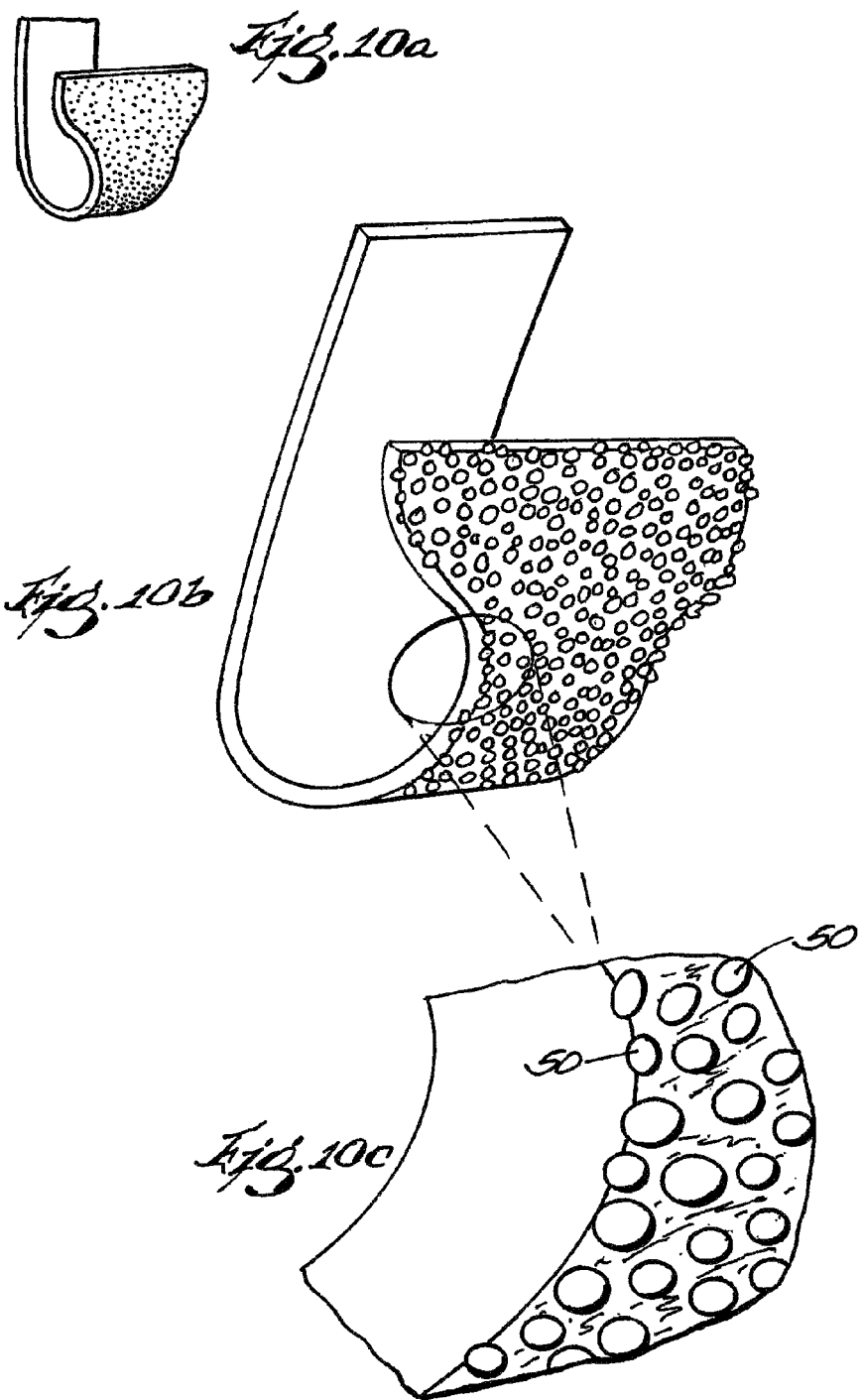

METHOD OF MAKING A CLIP FOR A SELF-LIGATING ORTHODONTIC BRACKET

CROSS-REFERENCE TO RELATED APPLICATIONS

This patent application is a continuation of U.S. patent application Ser. No. 11/697,312, filed Apr. 6, 2007, which claims priority to U.S. Provisional Patent Application No. 60/909,609, filed Apr. 2, 2007, and which is a continuation-in-part of and claims priority to U.S. patent application Ser. No. 10/592,184, filed on Sep. 8, 2006, which claims priority to International Application No. PCT/CA2005/000366, filed on Mar. 8, 2005, which claims priority to U.S. Provisional Application No. 60/551,281, filed on Mar. 8, 2004, the entire contents of all of which are hereby incorporated by reference.

FIELD OF THE INVENTION

The present invention relates to orthodontic brackets and, more particularly, to orthodontic brackets that are designed to have a surface color that blends into the patient's teeth so that the bracket is less noticeable.

BACKGROUND OF THE INVENTION

According to established orthodontic techniques, it is well known to attach an orthodontic bracket to a patient's tooth. The bracket provides a location for attaching an archwire and other orthodontic devices to facilitate movement of the tooth. According to established orthodontic techniques, it is well known to ligate an archwire to the orthodontic bracket utilizing an elastic or metal ligature. In conventional orthodontic brackets, the ligature is wrapped around respective gingival and occlusal tie wings so as to overlay the archwire at mesial and distal ends of the orthodontic bracket.

Typically, orthodontic brackets are made of a metallic material, such as stainless steel. These materials are commonly used because they are strong, non-staining, and relatively inexpensive. However, metallic materials can be cosmetically undesirable because they do not match the color of the patient's teeth, and thus the resulting brackets are very noticeable. To overcome the cosmetic difficulties noted above, manufacturers have developed brackets made from ceramic materials, such as polycrystalline alumina. These materials can be developed to closely match the color of the patient's teeth, thus resulting in a bracket that is less noticeable than common metal brackets.

Recently, designers have created self-ligating brackets that do not require a separate ligature for attachment of the archwire to the bracket. One type of self-ligating bracket is supplied with a clip that is movable between an open position, permitting access to the archwire slot, and a closed position, inhibiting access to the archwire slot. Self-ligating brackets substantially decrease the time involved in performing ligation procedures.

SUMMARY OF THE INVENTION

The present invention provides a self-ligating orthodontic bracket that is designed to have an exterior color that can be selected by the doctor or patient and can be different than the typical metallic color. In one aspect, the bracket of the present invention comprises a body having a lingual surface for attachment to a tooth and defining an archwire slot. The bracket further includes a clip movable between an open position, permitting access to the archwire slot, and a closed position, inhibiting access to the archwire slot. The clip comprises a base material and a coating that is designed to change the aesthetic characteristics of the base material. The base material can be made of any of a nuinber of different materials, such as chromium-cobalt, nickel-titanium, or stainless steel. The coating can be any of a number of different materials, such as composite resin hydroxyappatite, porcelain, epoxy, and lead free enamel paint. The coating can be applied to the base material by any of a number of different processes, including physical vapor deposition, chemical vapor deposition, painting, dipping, or spraying.

In one embodiment, the base material of the clip provides a treated (e.g., roughened) surface to enhance the attachment of the coating to the surface of the base material. For example, the surface of the base material can be laser etched, chemically etched, or mechanically etched. In one embodiment, the surface of the base material is etched to form undercuts that provide mechanical engagement of the coating to the surface of the base material. In another embodiment, the surface of the base material is provided by a mesh layer that is secured to the surface of the base material. For example, the mesh layer can be a metal mesh that is brazed to the surface of the base material. In yet another embodiment, the surface of the clip can be bombarded with particles to create micro-craters. In still another embodiment, the surface of the clip can be coated with micro-sintered balls. In a further embodiment, laser ablation can be used to create recesses or craters on the base material of the clip.

In a different embodiment of the present invention, the clip can be made using a polymeric material, such as polycarbonate, polyethylene, amplified polypropylene resin, and polyvinyl chloride. Preferably, the polymeric material is either clear or colored to match the tooth. For added strength, the clip can also include a reinforcing fiber (e.g., fiberglass or steel).

Other features and aspects of the invention will become apparent to those skilled in the art upon review of the following detailed description, claims, and drawings, wherein like elements have like numerals throughout the drawings.

BRIEF DESCRIPTION OF THE DRAWINGS

FIG. 1 is a perspective view of an orthodontic bracket embodying the present invention.

FIG. 2 is a perspective view of a second orthodontic bracket embodying the present invention.

FIG. 3 is a perspective view of a third orthodontic bracket embodying the present invention.

FIG. 4 is a partial perspective view of a clip that has been laser etched.

FIG. 5 is an enlarged detail of the clip of FIG. 4.

FIG. 6 is an enlarged detail of an alternative etching configuration.

FIG. 7 is a perspective view of a clip having a mesh layer attached to its surface.

FIG. 8 is an enlarged detail of the clip of FIG. 7.

FIGS. 9a and 9b illustrate a clip that has been bombarded with particles to produce a surface having micro-craters, and FIG. 9c illustrates the clip with a coating.

FIGS. 10a, 10b, and 10c illustrate a clip having micro-sintered balls on its surface.

FIG. 12b is an enlarged image of several recesses on the clip of FIG. 12a.

Figure 11:
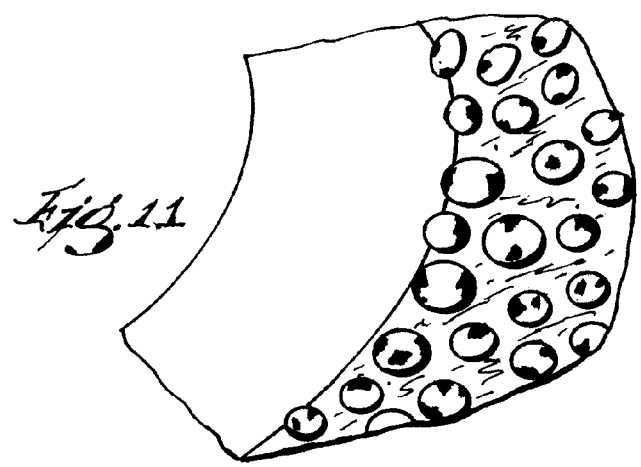
FIG. 11 illustrates a clip having micro-sintered balls that have been bombarded to produce micro-craters.

Before at least one embodiment of the invention is explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein is for the purpose of description and should not be regarded as limiting.

The use of "including", "having", and "comprising" and variations thereof herein is meant to encompass the items listed thereafter and equivalents thereof as well as additional items. The use of "consisting of" and variations thereof herein is meant to encompass only the items listed thereafter. The use of letters to identify elements of a method or process is simply for identification and is not meant to indicate that the elements should be performed in a particular order.

DETAILED DESCRIPTION

FIGS. 1-3 illustrate self-ligating orthodontic brackets 10 having a body 12, a mounting pad 14, a lateral insert 16, and a clip 18. Only the bracket of FIG. 1 will be described below, but a substantial portion of the following description generally applies to any of the brackets.

The mounting pad 14 includes a lingual surface 15 adapted to be connected to a labial surface of a tooth (not shown). The body 12 includes a lingual surface that is connected to a labial surface of the mounting pad 14. The body 12 defines gingival and occlusal directions and mesial and distal directions, as is known in the art. The body 12 includes two gingival tie wings 20 extending from the body 12 in the gingival direction and two occlusal tie wings 22 extending from the body 12 in the occlusal direction. The body 12 and the mounting pad 14 of the illustrated bracket 10 are made from a ceramic material (e.g., polycrystalline alumina) and are integrally formed with each other. Alternatively, the body 10 and mounting pad 12 can be separate from each other while remaining within the scope of the present invention. The separate body 12 and mounting pad 14 can be connected by an adhesive, resin, weld, or other connecting method known by those of ordinary skill in the art. In addition, the body 12 and the mounting pad 14 could be made from other materials such as ceramic, polymers, resins, metals, or the like.

The illustrated clip 18 is made from a chromium-cobalt base material and a porcelain coating. The base material is designed to provide the flexibility required for the clip to move between the open and closed positions, and to provide the strength to engage the archwire and provide movement to the tooth. The surface is oxidized during the heating process required for porcelain to enhance adhesion of the coating. As an alternative to chromium-cobalt, it is anticipated that other materials could be used, such as nickel-titanium, or stainless steel.

To enhance to attachment of the coating, the base material is roughened. Referring to FIGS. 4-5, the base material is laser etched to form undercuts 24 in the surface 26 of the base material. The undercuts provide an increased surface area and a mechanical engagement between the base material and the coating (not shown in FIGS. 4-5). FIG. 6 illustrates an alternative etching configuration having parallel walls 28 on the sides of the groove formed by the etching procedure. Instead of laser etching, chemical or mechanical etching, or a combination of the above could be used.

As an alternative to etching, the surface of the base material could be provided with a mesh layer 30. The mesh layer illustrated in FIGS. 7-8 comprises a metal mesh that is brazed to the surface of the base material. The mesh layer is provided on exposed surfaces of the clip 18, such as the labial surfaces of an engaging portion 32 and a guide portion 34 of the clip 18. In this embodiment, it is believed that a composite resin coating or an epoxy coating (not shown in FIGS. 7-8) will provide good results.

In one embodiment, aluminum oxide bombardment is used to create micro-craters 40 in the clip surface, as shown in FIGS. 9a-9c. A second bombardment with coated particles leaves the micro-craters with a silicon dioxide coating 42. The surface of the clip is then primed with a silane coating followed by a resin bonding 44 (e.g., BisGMA methylmethacsylote), as shown in FIG. 9c, which can be colored to provide the desired aesthetic result. The resin bonding 44 is more flexible, for example, than porcelain coating, and thus is more tolerant of metal flexing.

Another process for pretreating the surface of the clip involves the use of protrusive micro-sintered balls 50 that are secured to the surface of the metal clip, as shown in FIGS. 10a-10c. The micro-sintered balls create a textured surface having a greatly magnified surface area (as much as 200% greater). Cosmetic coating (e.g., a resin bonding) can then be applied over the sintered surface, where it will be firmly held in place. For enhanced adhesion, the surface having micro-sintered balls 50 can be bombarded with aluminum oxide particles and silicon dioxide particles (see FIG. 11), and then primed with a silane coating followed by resin bonding, as described above in connection with FIGS. 9a-9c.

The coating is designed to provide the ability to create a self-ligating bracket having colors, such as the color of a tooth. The coating can also provide corrosion resistance and a smoother feel to the patient. In the embodiment of FIG. 1, the porcelain coating is applied to the base material when the base material is hot. The coating can be applied by PVD, CVD, painting, spraying, dipping, or other suitable process depending on the material.

Instead of porcelain, it is believed that the coating could include hydroxyappatite, epoxy, or enamel paint. It is preferred that these materials would be substantially free of lead. The enamel paint or epoxy could be applied by electrostatic spraying, and a varnish sealant can then be applied.

Instead of the above-described coated clip, the clip could instead be made of a polymer material, such as a clear high-density polyurethane. This clip provides the required aesthetics by allowing the body to be viewed through the clip. The clip will benefit from the addition of strengthening fibers, such as fiberglass, carbon fiber, or Kevlar. In addition, the clip could be colored to almost any desired color. Instead of polyurethane, the clip could comprise polycarbonate, poly (ethylene-co-terepthalate resin), amplified polypropylene resin, and polyvinyl chloride. Any of these alternative materials could benefit by the addition of fiber reinforcement.

In alternative embodiments, as shown in FIGS. 12a-12i, laser ablation is used to create recesses or craters on the base material of the clip 18. The laser pulses or laser shots are directed onto the surface 26 of the base material to generate a roughened surface texture.

Generally, the laser shots can be applied to the surface 26 of the base material at generally any angle greater than 0 degrees with respect to the portion of the surface 26 to which the laser shots are applied. FIGS. 12a-12i illustrate several examples of the laser ablation process in which laser shots are applied at different angles with respect to the surface 26. It should be understood that, in accordance with the present laser ablation process, virtually unlimited actual resulting recess arrangements may be provided on the surface 26 of the base material.

In one example, a mode-locked Nd:YAG (neodymium-doped yttrium aluminum garnet) laser (not shown) is used, and the laser is capable of generating laser pulses of 8 million Joule, 30 picosecond duration, and 355 nm wavelength with a repetition rate of 30 Hz. It should be understood that, other suitable lasers and/or different laser operating parameters known by those of ordinary skill in the art could also be used.

Figure 12A:
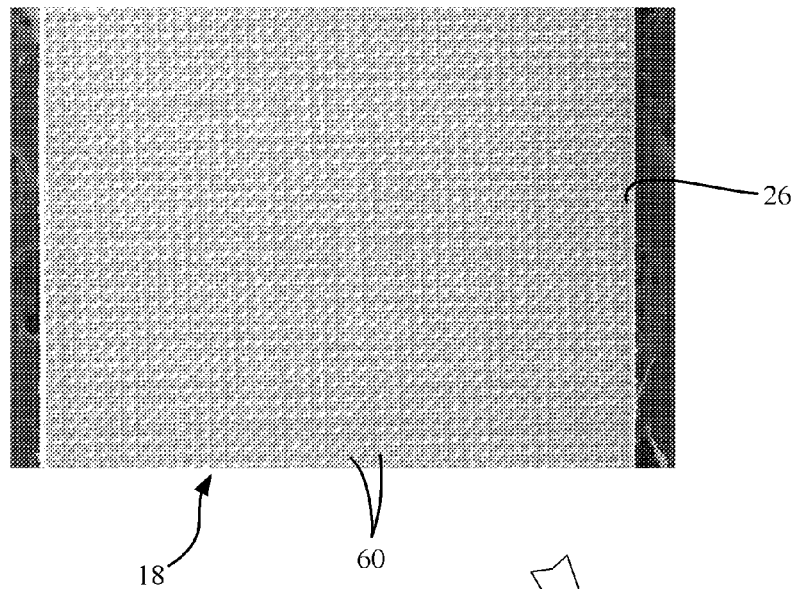
FIG. 12a is an image of a portion of a self-ligating orthodontic clip having recesses formed by generally perpendicular laser ablation.
Figure 12B:
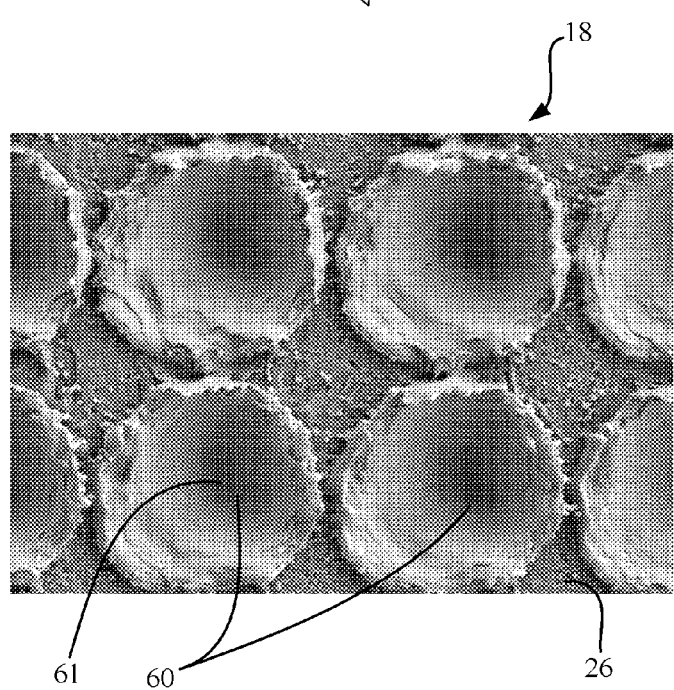

FIG. 12b illustrates a texture of the surface 26 of the base material viewed with a Hitachi field-emission gun scanning microscope and Sensofar optical imaging profilometer. In this example, the laser pluses are generated and are directed onto the base material at an angle substantially perpendicular or normal to the surface 26 of the base material (e.g., at about 90 degrees). A number of laser shots are directed at a location 61 on the surface 26 to create an associated crater 60. Additional laser shots are directed at other locations 61 on the surface 26 of the base material at a predetermined distance with respect to each other to arrange the craters 60 generally in rows with a step size (spacing).

In the example illustrated in FIG. 12b, the laser pulses are generated at 0.12 million Joule per pulse. The additional laser pulses are directed at the other locations 61 at a predetermined step size of, for example, 35 micrometer. In the example, 15 laser shots are used at each location 61 to create the associated crater 60.

It should be understood that more or fewer than 15 laser shots could be used to form each crater 60. It should also be understood that the parameters of the laser shots, such as, for example, the pulse duration, energy, optical wavelength, focal spot diameter, and/or the step size could be varied.

In another example, the laser shots are substantially perpendicularly applied (e.g., at about 90 degrees) on the surface 26 of the base material, and each crater 60 is formed by ten laser shots on the associated location 61. The surface 26 of the base material has a roughness of about 0.4 micrometer before the laser ablation. After the laser ablation, some of the base material is splattered around the crater 60 and is about 2 micrometers above the surface 26, and the bottom of the crater 60 is about 5 micrometer below the surface 26. As such, in this example, a roughness of about 7 micrometer is provided on the surface 26 of the base material by 10 laser shots on each crater 60.

The laser treatment increases the roughness of the surface 26 of the base material, and the depth of a crater 60 generally increases with the number of the laser shots applied thereon. Specifically, in one example, the depth of the crater 60 could increase from, for example, about 3 micrometer to about 5 micrometer, and further to about 8 micrometer, when the number of the laser shots at the associated location 61 increases from 5 shots to 10 shots, and further to 15 shots, respectively.

Figure 12C:
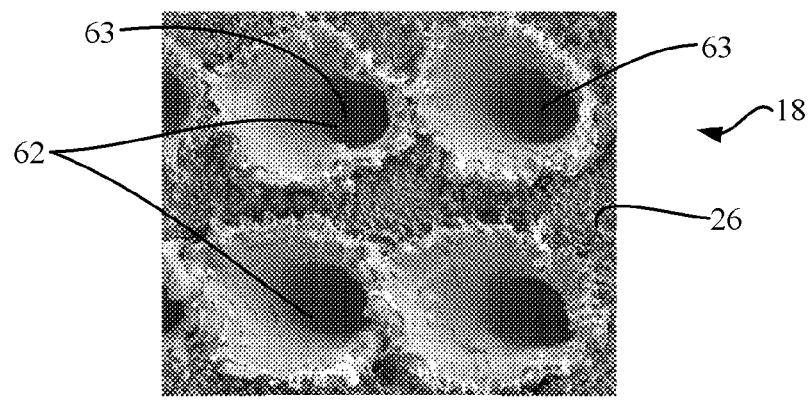
FIG. 12c is an image of a clip having recesses formed by angled laser ablation.
Figure 12D:
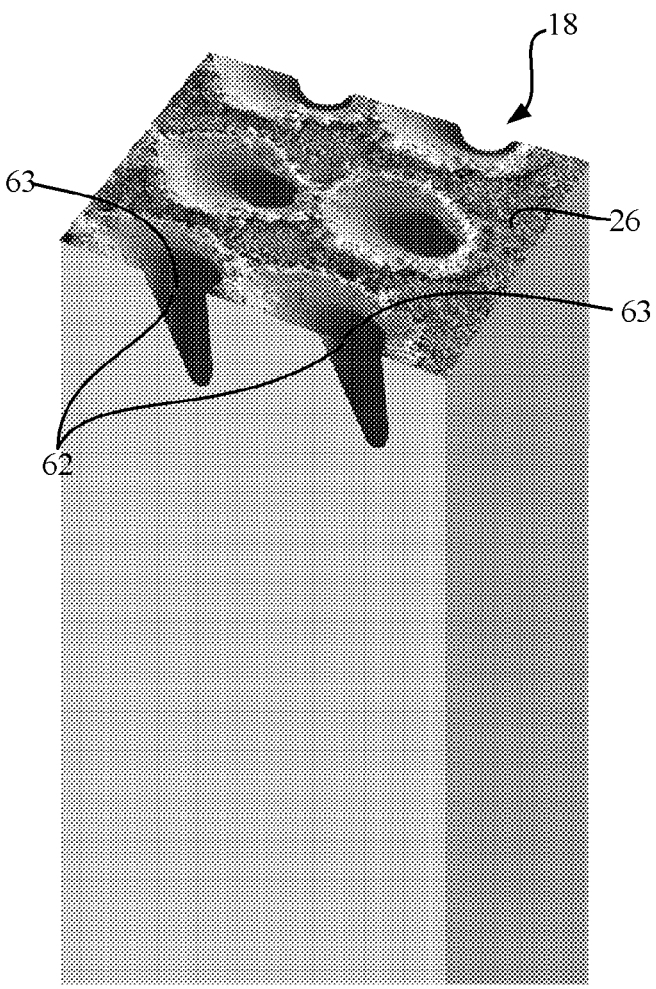
FIG. 12d is a partial cross-sectional profile of some of the recesses of the clip of FIG. 12c.
Figure 12E:
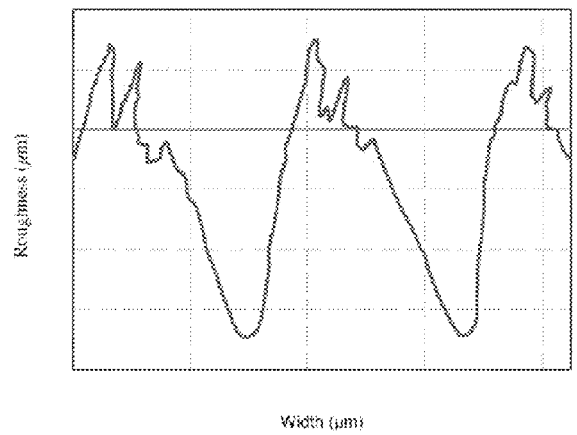
FIG. 12e is a schematic view of the profile of the recesses of FIG. 12d.

In an alternative embodiment, shown in FIGS. 12c-12e, laser shots are directed at an angle which is not perpendicular and not normal (less than 90 degrees) with respect to the surface 26 of the base material (a "non-normal angle"). In some examples, the non-normal angle is between about 15 to about 75 degrees with respect to the surface 26 of the base material, and, in other examples, the non-normal angle is between about 25 to about 65 degrees. In the example illustrated in FIG. 12e, the non-normal angle is about 45 degrees with respect to the surface 26 of the base material.

In this embodiment, the laser shots are directed on each location 63 to form an associated crater 62. By applying angled laser shots onto the surface 26 of the base material, each crater 62 is formed as a generally oval-shaped opening and creates an undercut into the base material. The angled laser ablation on the surface 26 of the base material increases the adhesion of the coating with respect to the base material by enhancing the mechanical interlock between the coating material and the base material.

In the example illustrated in FIGS. 12c-12e, the laser pulses are generated at 0.25 million Joule per shot. The craters 62 are arranged with a step size of 50 micrometer, and twenty laser shots are used at each location 63 to create the associated crater 62.

In further embodiments, as shown in FIGS. 12f-12i, the laser shots are directed multi-laterally onto the clip 18. The use of the term "multi-laterally" is not intended to limit the scope of this embodiment to encompass only laser shots from opposite sides. Instead, the scope of this embodiment encompasses other multi-directional arrangements and other multi-angular orientations of the laser shots.

Figure 12F:
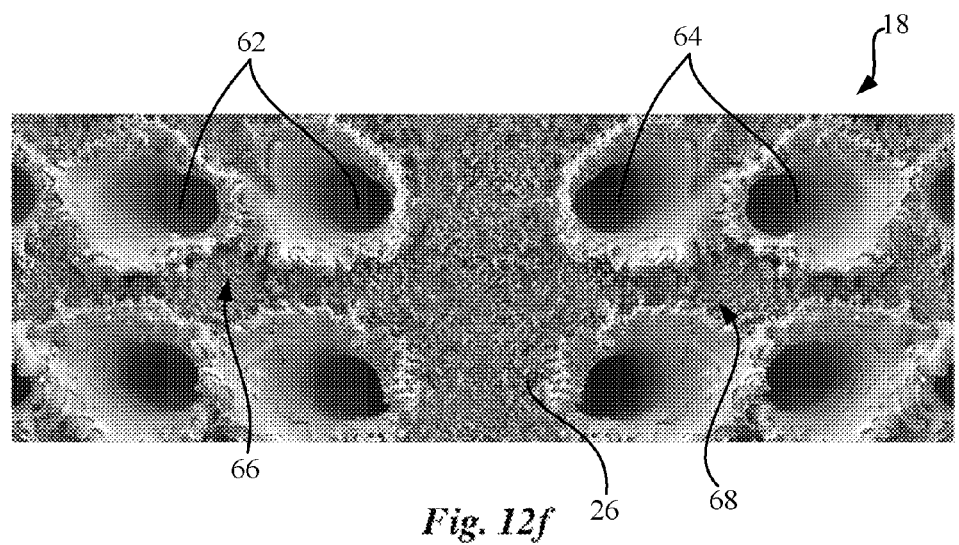
FIG. 12f is an image of a clip having recesses formed by multi-lateral, angled laser ablation.
Figure 12I:
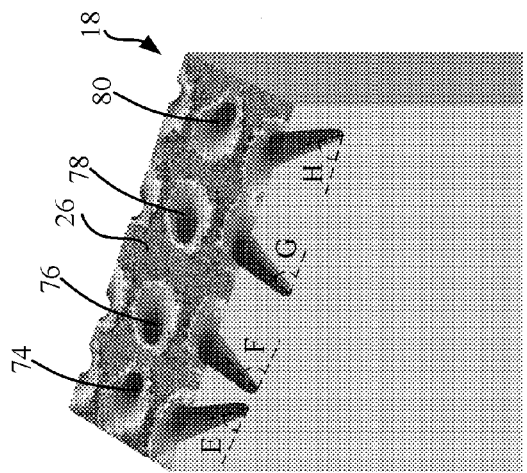
FIG. 12i is a partial cross-sectional profile of a clip having recesses formed by angled laser ablation of still another embodiment.
Figure 12H:
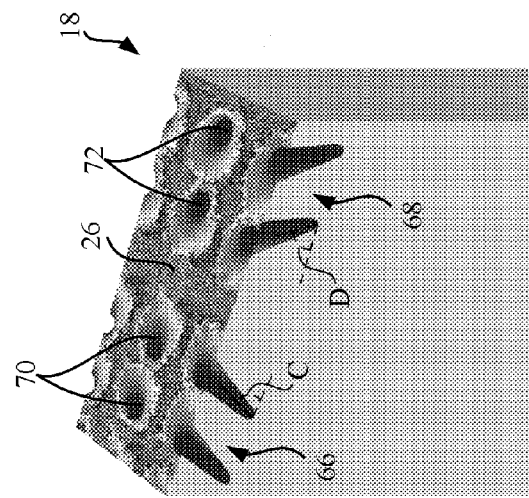
FIG. 12h is a partial cross-sectional profile of a clip having recesses formed by angled laser ablation of another embodiment.
Figure 12G:
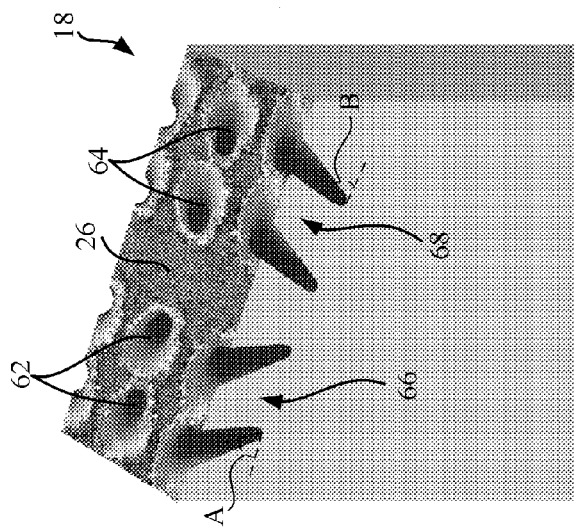
FIG. 12g is a partial cross-sectional profile of some of the recesses of the clip of FIG. 12f.

In the embodiment illustrated in FIGS. 12f and 12g, laser shots are directed at a first non-normal angle A from one side (e.g., about 45 degrees from the left side) onto the surface 26 of the base material to form a first group of the craters 62. Laser shots are also directed at a different second angle B from another direction (e.g., about 45 degrees from the right side) onto the surface 26 of the base material to form a second group of craters 64. As shown in FIG. 12g, the craters 62, 64 have a generally conical shape. The craters 62 and 64 are respectively arranged on a first portion 66 and, in the illustrated example, an adjacent second portion 68 of the surface 26. The craters 62, 64 generally open away from each other. As such, the craters 62 are defined on the surface 26 of the base material at an angle different than that of the craters 64.

In another embodiment, as shown in FIG. 12h, craters 70, 72 having different angles (angles C and D, respectively) are arranged side by side on the surface 26, and the craters 70, 72 generally open toward each other. In the illustrated embodiment, the angle C is about 45 degrees from the right side, and the angle D is about 45 degrees from the left side.

With respect to FIGS. 12f-h, it should be understood that the craters 62, 64 or 70, 72 could be arranged in other ways, such as for example, in alternative rows or columns on the surface 26.

In still another embodiment, as shown in FIG. 12i, craters 74, 76, 78, 80 are randomly arranged on the surface 26 at different angles (angles E, F, G and H, respectively) and generally without a pattern.

In other embodiments, the laser shots can be directed onto the surface 26 of the base material at other different angles to form the craters 62, 64. Also, craters could be defined on the surface 26 of base material at more than two different angles, including normal and non-normal angles, along different axes, and/or in groups along different planes. In addition, more than two groups of craters could be created on the surface 26 of the base material. The groups could be formed as, for example, alternating rows, columns, sections, combinations, etc. arranged laterally, vertically, diagonally, combinations on the surface 26 of the base material.

In the illustrated examples, the laser shots are used at a relatively low energy level which facilitates using a cheaper laser with a high rate of repetition. The craters defined on the surface 26 of the base material, and especially the craters defined with different angles, facilitate adhesion of the coating to the base material.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described herein are further intended to explain best modes known for practicing the invention and to enable others skilled in the art to utilize the invention in such, or other, embodiments and with various modifications required by the particular applications or uses of the present invention.

I claim:

1. A method of making a clip for a self-ligating orthodontic bracket, the method comprising:
    creating a clip base from a base material, wherein the base material of the clip base has a surface;
    creating multiple conically shaped recesses on the surface of the base material of the clip base using laser ablation, wherein creating recesses includes directing a plurality of laser shots on an associated location on the base material of the clip base to form each of the conically shaped recesses and creating at least one crater on the surface of the base material of the clip base, creating at least one crater including depositing material from an associated recess onto the surface of the base material of the clip base adjacent the associated recess; and
    after creating recesses, applying a coating to at least a portion of the base material of the clip base to cover at least one of the craters and associated recesses to create a coated clip.

2. The method of claim 1, wherein creating recesses includes creating a first group of recesses each having an axis oriented at a first angle with respect to the surface of the base material of the clip base and creating a second group of recesses each having an axis oriented at a second angle with respect to the surface of the base material of the clip base, the first angle being different than the second angle.

3. The method of claim 2, wherein at least one of creating a first group and creating a second group includes creating the first group adjacent to the second group.

4. The method of claim 1, wherein the base material of the clip base has a surface, the recesses being formed on the surface of the base material of the clip base, and wherein creating recesses includes creating at least one of the recesses having an axis oriented at a non-normal angle with respect to the surface of the base material of the clip base to form an undercut in the surface of the base material of the clip base.

5. The method of claim 1, wherein applying a coating includes applying a coating comprises a material selected from the group consisting of porcelain, epoxy, enamel, and hydroxyappatite.

6. The method of claim 1, wherein creating recesses includes creating at least one of the recesses having an axis oriented at about 45 degrees with respect to the surface of the base material of the clip base.

* * * * *